(12) United States Patent
Ryan et al.

(10) Patent No.: US 7,530,546 B2
(45) Date of Patent: May 12, 2009

(54) SWABBABLE NEEDLE-FREE INJECTION PORT VALVE SYSTEM WITH ZERO FLUID DISPLACEMENT

(75) Inventors: Dana Wm. Ryan, Nolensville, TN (US); David P. Gordon, Stamford, CT (US); James M. Kaiser, Austin, TX (US); Frank A. Scarfone, Miramar, FL (US)

(73) Assignee: Rymed Technologies, Inc., Franklin, TN (US)

( * ) Notice: Subject to any disclaimer, the term of this patent is extended or adjusted under 35 U.S.C. 154(b) by 183 days.

(21) Appl. No.: 11/341,119

(22) Filed: Jan. 26, 2006

(65) Prior Publication Data

US 2006/0118749 A1 Jun. 8, 2006

Related U.S. Application Data

(63) Continuation-in-part of application No. 10/756,601, filed on Jan. 13, 2004, now Pat. No. 6,994,315.

(51) Int. Cl.
*F16K 51/00* (2006.01)
*F16L 29/00* (2006.01)
*F16L 37/28* (2006.01)

(52) U.S. Cl. .................... 251/149.6; 604/905
(58) Field of Classification Search ............... 251/149.1, 251/149.4, 149.6; 604/905
See application file for complete search history.

(56) References Cited

U.S. PATENT DOCUMENTS

| | | | |
|---|---|---|---|
| 4,440,207 A | 4/1984 | Genatempo et al. | |
| 4,610,469 A | 9/1986 | Wolff-Mooij | |
| 5,065,783 A | 11/1991 | Ogle, II | |
| 5,147,329 A | 9/1992 | Brannon | |
| 5,242,432 A | 9/1993 | DeFrank | |
| 5,251,873 A | 10/1993 | Atkinson et al. | |
| 5,269,771 A | 12/1993 | Thomas et al. | |
| 5,360,413 A | 11/1994 | Leason et al. | |
| 5,380,306 A | 1/1995 | Brinon | |
| 5,439,451 A | 8/1995 | Collinson et al. | |
| 5,470,319 A | 11/1995 | Mayer | |
| 5,492,147 A | 2/1996 | Challender et al. | |
| 5,518,005 A | 5/1996 | Brannon | |
| 5,520,666 A | 5/1996 | Choudhury et al. | |
| 5,533,708 A * | 7/1996 | Atkinson et al. | 251/149.1 |
| 5,536,258 A | 7/1996 | Folden | |
| 5,549,577 A | 8/1996 | Siegel et al. | |
| 5,616,129 A | 4/1997 | Mayer | |
| 5,618,268 A | 4/1997 | Raines et al. | |
| 5,645,538 A | 7/1997 | Richmond | |
| 5,658,260 A | 8/1997 | Desecki et al. | |
| 5,685,866 A | 11/1997 | Lopez | |
| 5,694,686 A | 12/1997 | Lopez | |
| 5,741,121 A | 4/1998 | O'Leary | |
| 5,806,831 A | 9/1998 | Paradis | |

(Continued)

*Primary Examiner*—John K Fristoe, Jr.
(74) *Attorney, Agent, or Firm*—Gordon & Jacobson, PC

(57) ABSTRACT

An improved needle-free intravenous injection port assembly is disclosed. Embodiments include a boot valve with a helical surface, a boot valve and septum which mate with mechanical interference, a spike with a rough outer surface coated with a lubricant, a septum having a shoulder and a single continuous swabbable surface, a septum and a boot valve which are pre-punctured, a septum with a frustroconical extension and a combination single piece septum and boot valve. The injection port assembly provides zero fluid displacement during coupling and uncoupling.

6 Claims, 19 Drawing Sheets

U.S. PATENT DOCUMENTS

| | | |
|---|---|---|
| 5,839,715 A | 11/1998 | Leinsing |
| 5,957,898 A | 9/1999 | Jepson et al. |
| 6,113,068 A | 9/2000 | Ryan |
| 6,506,182 B2 | 1/2003 | Estabrook et al. |
| 6,699,229 B2 | 3/2004 | Zinger et al. |
| 6,802,490 B2 | 10/2004 | Leinsing et al. |
| 6,994,315 B2 | 2/2006 | Ryan et al. |

* cited by examiner

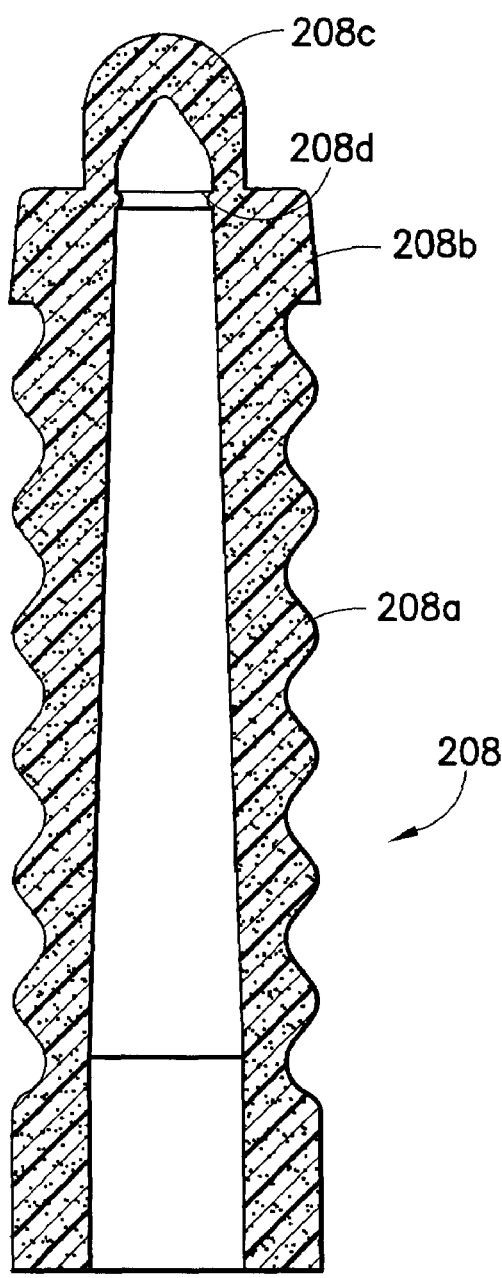
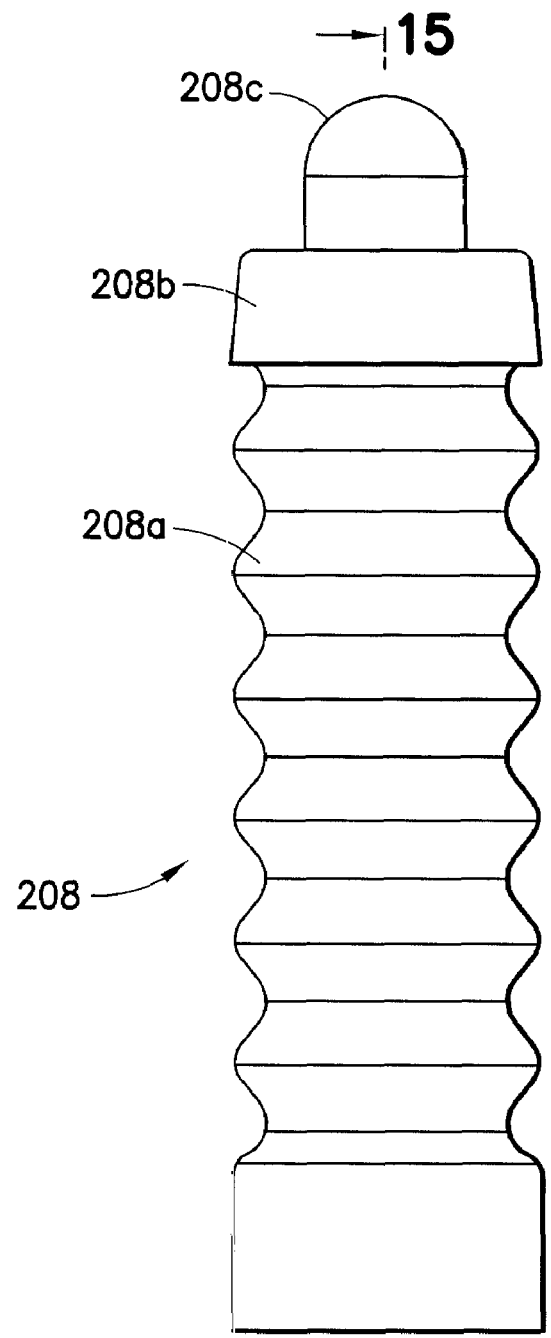
FIG. 15
FIG. 14

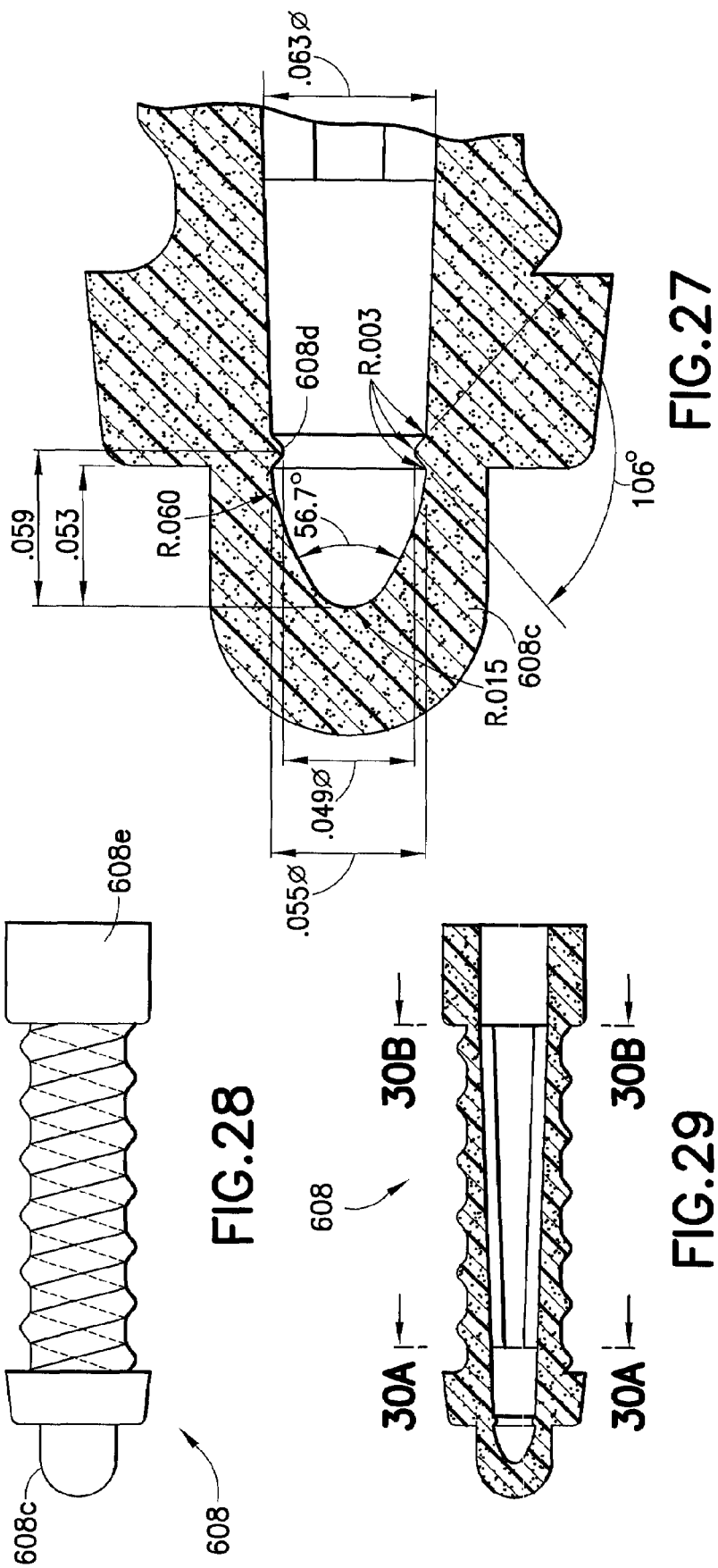

SWABBABLE NEEDLE-FREE INJECTION PORT VALVE SYSTEM WITH ZERO FLUID DISPLACEMENT

This application is a continuation-in-part of U.S. Ser. No. 10/756,601 filed Jan. 13, 2004, now U.S. Pat. No. 6,994,315 the complete disclosure of which is incorporated herein by reference. This application also relates to U.S. Pat. No. 6,113,068 the complete disclosure of which is hereby incorporated by reference herein.

BACKGROUND OF THE INVENTION

1. Field of the Invention

This invention relates to medical intravenous administration line connectors. More particularly, this invention relates to needle-free intermittent injection ports for the safe infusion and/or aspiration of fluids in intravenous and blood administration therapy.

2. State of the Art

Intravenous fluid therapy for parenteral administration or blood sampling in healthcare facilities routinely uses intermittent injection port connectors. These connectors or adapters are connected to a vascular access device such as a peripherally inserted central venous catheter (PICC), central venous catheter (CVC), femoral catheter, Huber needle for implantable ports, peripheral intravenous catheter (PIV), catheter and intravenous extension set, or intravenous administration set. The intermittent injection port connector allows the infusion therapist a means to infuse fluids or aspirate the patient's blood through the connector without having to stick the patient with a needle each time.

Traditionally, healthcare providers worldwide have used an intermittent injection port connector utilizing a latex septum or barrier requiring a hollow steel needle attached to a syringe or intravenous line set to pierce the resilient latex septum opening up a fluid channel to the patient. Since the discovery in the mid-1980's of the virus that causes AIDS, and the possibility of this virus being transmitted to the healthcare provider via an accidental needlestick injury, a major change within the medical device industry has taken place. Although hepatitis B and C are still the leading concern among healthcare professionals via an accidental needlestick injury, the emotional concern of the possibility of contracting AIDS through contaminated needles has been the catalyst for change in the industry.

Since the mid 1980's, various design innovations have solved the accidental needlestick injury crisis among healthcare professionals. However, two critical catheter management issues have been on the rise; i.e., interluminal thrombotic catheter occlusions, and catheter related blood stream infections (CRBSIs). Now that healthcare professionals are comfortable that they are protected from accidental needlestick injuries when they use these types of safety injection port systems, they are beginning to focus on the patient safety aspects of these products; i.e., to overcome occlusions and CRBSIs. It is clear that a new generation of intermittent injection port designs is needed to improve and resolve concerns such as microbial ingress, ineffective patient fluid pathway protection, negative fluid displacement retrograding blood up into the catheter lumen, septum seal integrity, and other critical functional features.

Co-owned U.S. Pat. No. 6,113,068 focuses on improving upon the critical microbial barrier performance and functional attributes important for overall patient safety. After manufacture, it effectively provides a single piece injection port with standard male-luer connectors, i.e. universal access. No extra adapters, components, or end caps are required, thereby reducing the overall cost to deploy the system throughout the healthcare facility. The upper septum is swabbable and easy to disinfect. There are no gaps between the septum and the outer body opening, thereby improving septum seal integrity. This prevents gross particulate contamination from entering into the internal body of the valve, thereby minimizing downstream contamination. The injection port cannot be used with non-safety hollow bore needles, thereby complying with OSHA guidelines and mandates. The double microbial barrier design is an effective barrier to pathogen ingress. The combination of the double resilient barriers (the upper resilient septum and the lower resilient boot valve) and their association with the hollow bore spike and centering component significantly reduce the negative fluid displacement to a negligible 0.0035 mL, which is significantly reduced relative to all other currently available needle-free connector systems. The plastic centering component captures both barriers allowing the double barriers to move freely along the inner wall of the outer body and to keep the slits axially aligned with the spike tip and shaft. The straight-through fluid path eliminates the tortuous paths found in many prior art devices. Priming volume is reduced to only 0.034 mL of fluid which is one of the smallest volumes for swabbable injection port connectors. Activation force to fully access the valve is approximately 5.5 lbs, an acceptable amount for the clinician while providing excellent snap-back and resealing characteristics. In the device described in my prior patent, fluid flow at gravity averaged 7,500 mL per hour thereby exceeding the ISO standard of 6,000 mL per hour with the fluid source at one meter above the valve. In the manufacturing process, after assembly of all the components and the sonic-welding of the two outer bodies, an ISO male luer fixture could be used to initially pre-puncture the two silicone barriers. As the male luer fixture is attached to the injection port assembly, the internal spike punctures the two silicone barriers and distributes the liquid silicone lubricant along the puncture axes in the two barriers.

Although the invention which is described in U.S. Pat. No. 6,133,068 improved upon many of the desired patient safety attributes for a swabbable injection port connector system, the prior design may be improved.

SUMMARY OF THE INVENTION

It is therefore an object of the invention to provide a needle-free medical valve injection port which is safe, efficacious, and easy to use.

It is also an object of the invention to provide an injection port valve system which is swabbable and provides an excellent microbial ingress barrier protection.

It is another object of the invention to provide an injection port valve system which has less than 0.002 mL fluid displacement during both the "connection to" and "disconnection from" the medical valve.

It is an additional object of the invention to provide an injection port valve system which has a zero fluid displacement to minimize blood being refluxed or retrograded into a vascular access device lumen during both the "connection to" and "disconnection from" the medical valve. For purposes herein, the term "zero fluid displacement" is defined as fluid displacement of 0.000 mL with a small tolerance of ±0.002 mL upon attachment (connection) and detachment (disconnection) of the port valve system from a line connector.

It is a further object of the invention to provide an injection port valve system which has improved snap-back characteristics in repeated use over the life cycle of the product to minimize fluid leakage and/or microbial ingress.

Another object of the invention is to provide an injection port valve system which minimizes dead space within the fluid pathway thereby reducing the probability of downstream contamination and improving the flushing capabilities of the medical valve.

A further objective of the invention is to provide an injection port valve system which has excellent leak resistant characteristics of repeated use during its life cycle.

An additional object of the invention is to provide an injection port valve system which improves the lubrication of the spike shaft, spike tip, and the puncture axis geometry to minimize coring of the two resilient microbial barriers during repeated use.

Yet another object of the invention is to provide an injection port valve system which has improved back-pressure leak resistant capabilities.

It is even a further object of the invention to provide an injection port valve system which is easy to use and activate by reducing the overall activation force required.

In accord with these objects, which will be discussed in detail below, an injection port valve system according to the invention has five total components: an upper plastic outer body with ISO compliant threads ("the female luer body"), a lower plastic outer body with an integrally formed unitary hollow spike and an ISO compliant male luer lock in fluid communication with the spike ("the spike body"), an upper resilient barrier ("the septum"), a plastic centering and barrier cage ("the H-guide"), and a lower resilient barrier ("the boot valve").

The septum and the boot valve are designed to minimize fluid leakage from the patient side of the valve at high pressure (e.g. when the IV tubing is kinked or clogged) and to prevent microbial ingress from the outside environment into the patient's bloodstream. The septum and the boot valve are joined at the H-guide. The valve also includes a hollow spike having an open tip. The spike preferably has a bullet-nose bridge structure with at least two fluid opening channels or an unobstructed opening. The boot valve completely covers the spike giving the valve the first barrier of defense against fluid leakage to the outside environment and the second barrier of defense against microbial ingress from the outside environment into the patient's bloodstream. The septum provides the first barrier of defense against microbial ingress from the outside environment into the patient's bloodstream, and the second barrier of defense against fluid leakage to the outside environment. There is no dead space between the septum and the boot valve. There is also no dead space between the spike tip bridge and the inner wall of the boot valve. According to one embodiment, there is an internal ring seal protruding from the inner wall of the boot valve positioned just below the spike tip opening that has an interference fit with the spike shaft to prevent fluid blow-by down the outer surface of the spike. There is preferably an interference fit between the septum and the boot valve, as well as an interference fit between the H-guide and the two resilient barriers. The boot valve is sufficiently resilient to move the two resilient barriers and the H-guide immediately back to the original slightly compressed state upon the removal of a male luer connector from the female luer. The septum is preferably provided with an outer shoulder or flange, a tapered end facing the boot valve, a matching contour mating surface for mating with the boot valve, and a single continuous swabbable surface facing away from the boot valve and exposing the septum surface to the outside. The boot valve is preferably provided with a spring-like "helical" external surface. The septum and the boot valve are preferably pre-punctured with a knife blade having a width of approximately 0.056 inches which is lubricated with a fluorosilicone liquid formulation. The surface of the spike is preferably roughened and coated with a fluorosilicone lubricant.

The medical valve of this invention has many features; no single one is solely responsible for its improved microbial and functional attributes. The system achieves a zero fluid displacement and an improved microbial ingress barrier.

Additional objects and advantages of the invention will become apparent to those skilled in the art upon reference to the detailed description in conjunction with the accompanying drawings.

BRIEF DESCRIPTION OF THE DRAWING

FIG. 14 is a side elevational view of a second embodiment of a boot valve according to the invention;

FIG. 15 is a section taken along line 15-15 in FIG. 14;

FIG. 27 is a highly magnified view of the tip portion of the boot of FIG. 26 showing radii, angles and dimensions;

FIG. 28 is a side view of the boot of FIG. 26; and

FIG. 29 is a cross-sectional view of the boot of FIG. 26; and

FIGS. 30A and 30B are views of the inside surface walls of the boot at proximal and distal locations shown in FIG. 29.

DETAILED DESCRIPTION OF THE PREFERRED EMBODIMENTS

Figure 1:
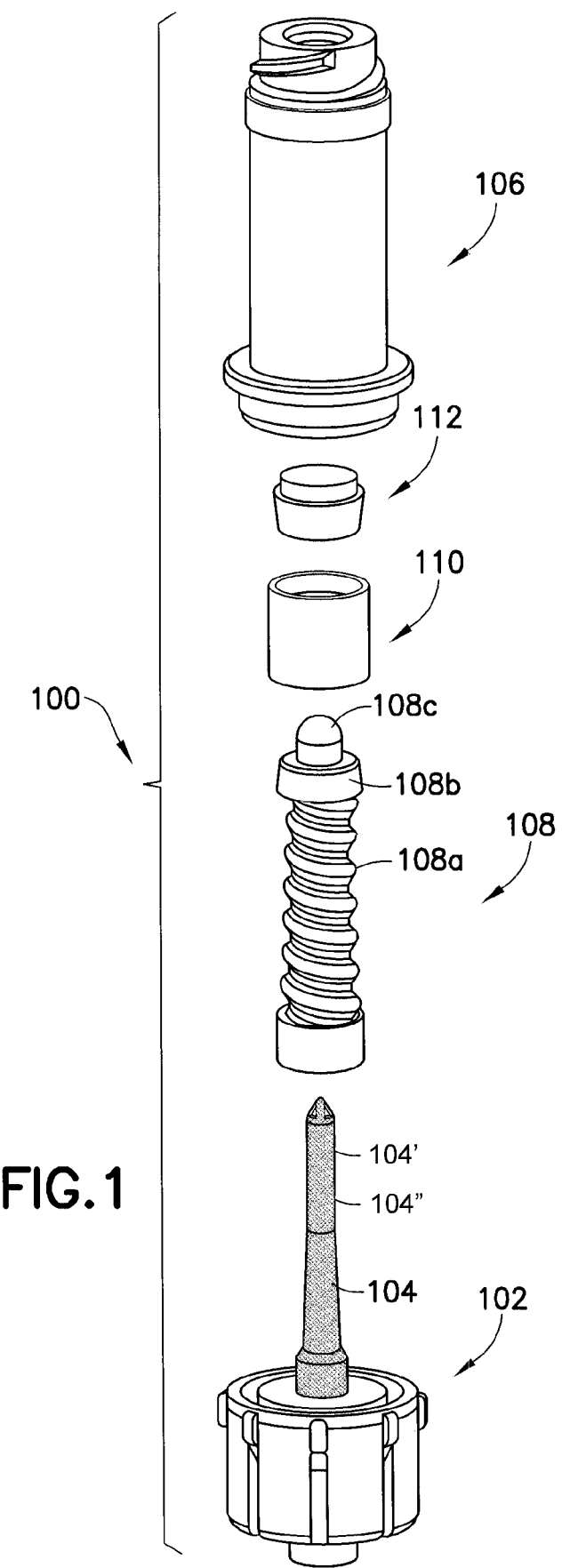
FIG. 1 is an exploded perspective view of a first embodiment of the invention.
Figure 2:
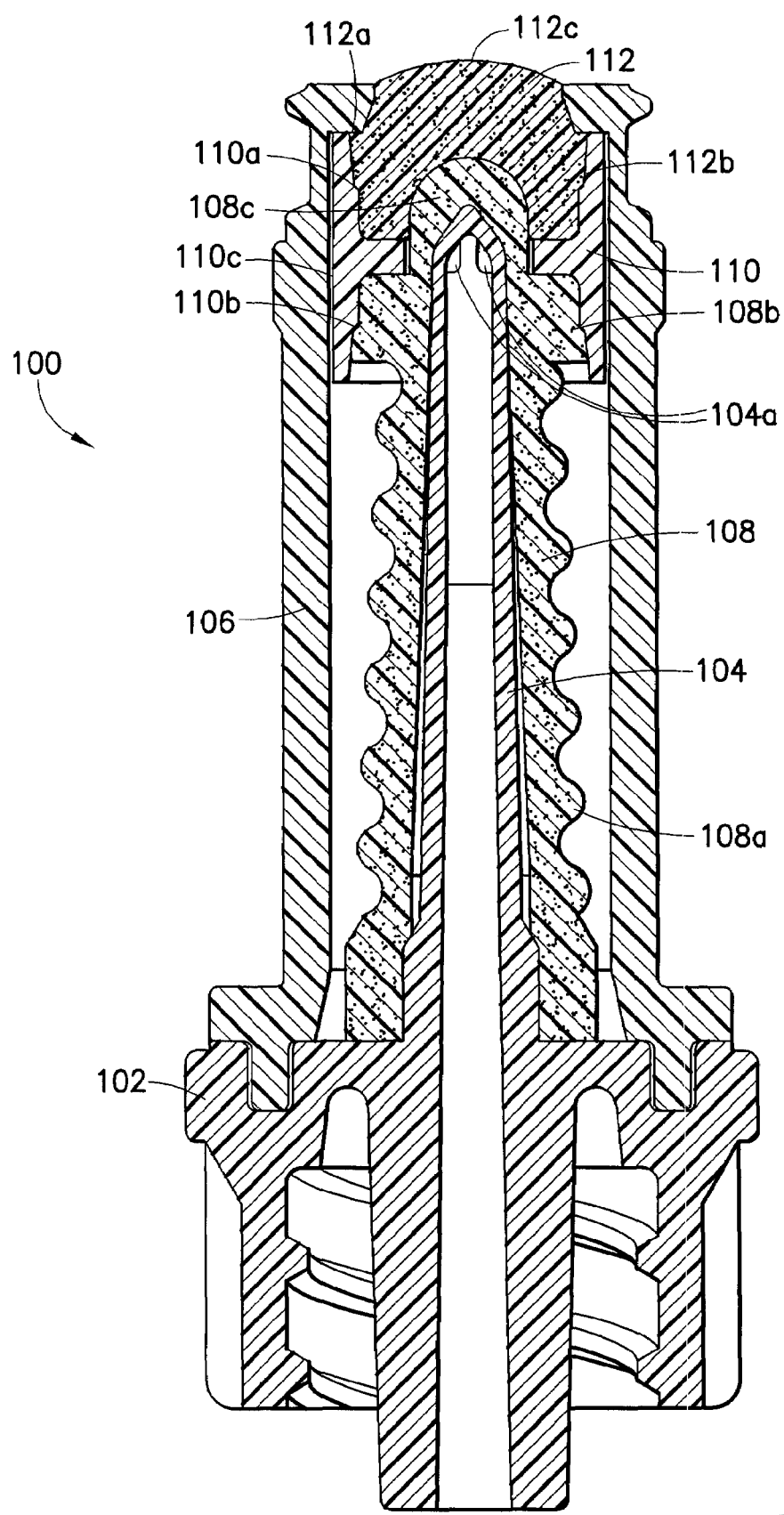
FIG. 2 is a longitudinal cross-sectional view of the assembled components of FIG. 1.
Figure 3:
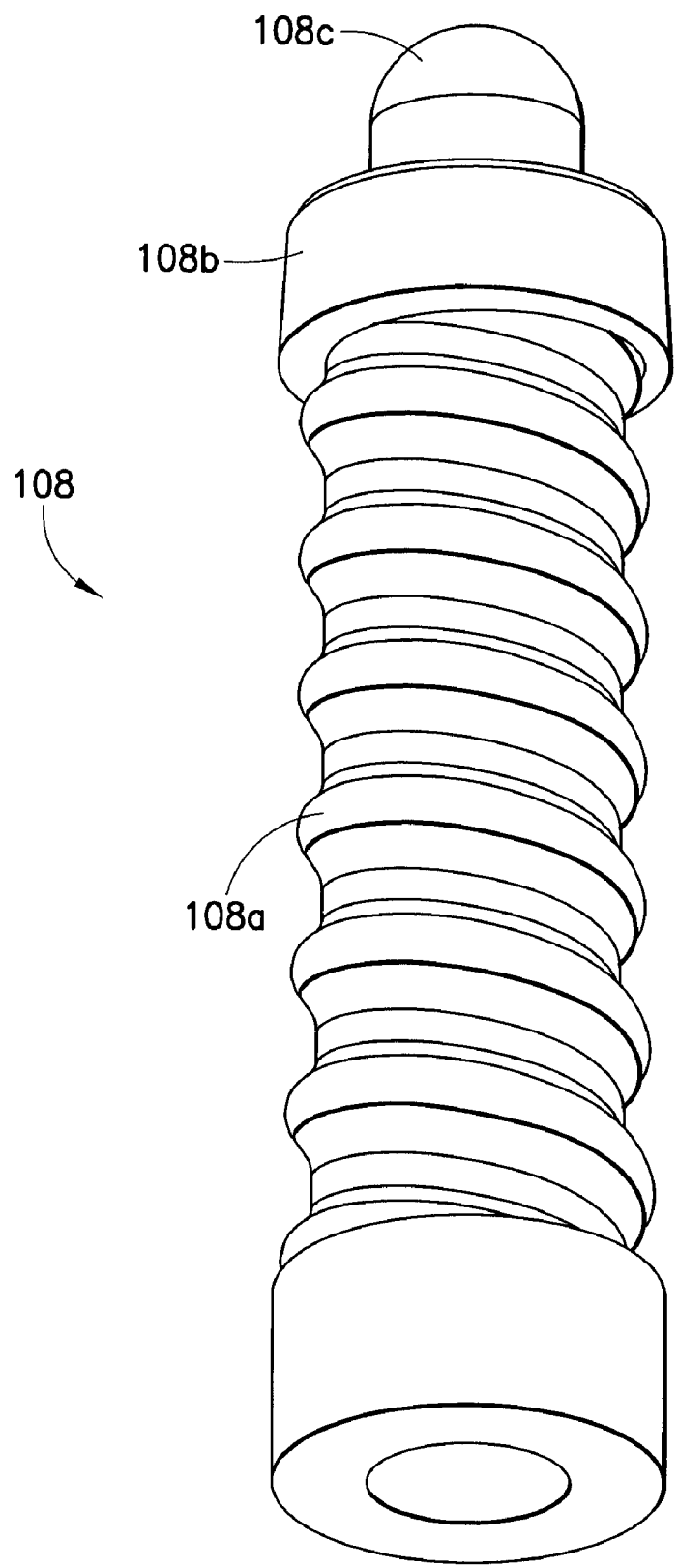
FIG. 3 is a perspective view of a first embodiment of a boot valve according to the invention.

Turning now to FIGS. 1-3, a first embodiment of a needle-free intravenous injection port assembly 100 according to the invention generally includes a spike body 102 provided with a hollow spike 104, a female luer connector component 106, a flexible and resilient boot valve 108, an H-guide centering member 110, and a resilient septum 112. As seen best in FIG. 2, the boot valve 108 extends over the spike 104, the H-guide 110 is provided over a portion of the boot valve 108, and the septum 112 is provided between the H-guide 110 and an end of the female luer connector component 106. The spike body 102 and the female luer connector 106 are preferably made from a hard plastic material such as polycarbonate and are welded, glued, or otherwise mated together during assembly of the assembly 100. The H-guide 110 is preferably made from a semi-rigid plastic such as high density polyethylene. The boot valve 108 and the septum 112 are preferably made from a rubber-like material, such as synthetic polyisoprene or silicone rubber, having an approximately 60-70 Shore A Durometer. The inside surface of the boot valve 108 is preferably roughened by EDMing the injection mold core pin. During assembly of the assembly 100, the septum 112 and boot valve 108 are compressed slightly, as the height of the female luer connector component 106 is slightly less than the height of the boot valve/septum combination up to the shoulder 112a of the septum 112. Thus, in an at-rest position, the boot valve is slightly compressed (as is the septum).

According to the illustrated embodiment and as shown in larger view in FIG. 3, the boot valve 108 is preferably configured with a helical external surface 108a and a radially enlarged portion 108b. The septum 112 is preferably provided with a shoulder 112a, a tapered end 112b facing the boot valve, and a single continuous swabbable surface 112c facing away from the boot valve as described in more detail below with reference to FIGS. 9 and 10. The septum and the boot valve are preferably pre-punctured with a knife blade having a width of 0.056" by aligning the septum and the boot valve in the H-guide in a subassembly and puncturing the septum and the boot valve in a pre-assembly manufacturing process as described below. The H-guide 110 is preferably provided with a tapered internal surface 110a, 100b at both ends and its outer surface 110c is polished very smooth as described in more detail below with reference to FIGS. 11-13. The surface 104' of the spike 104 is preferably roughened and is coated with a fluorosilicone lubricant 104". The roughened finish 104' may be achieved by several methods including, but not limited to, EDM, sandblasting, media blasting, chemical etching, mechanical means, etc. The roughened finish 104' helps to "entrap" the lubricant 104". The radially enlarged portion 108b of the boot valve 108 is preferably tapered to match the taper of the H-guide 110. The boot valve 108 and the septum 112 are preferably mated with mechanical interference.

Figure 4:
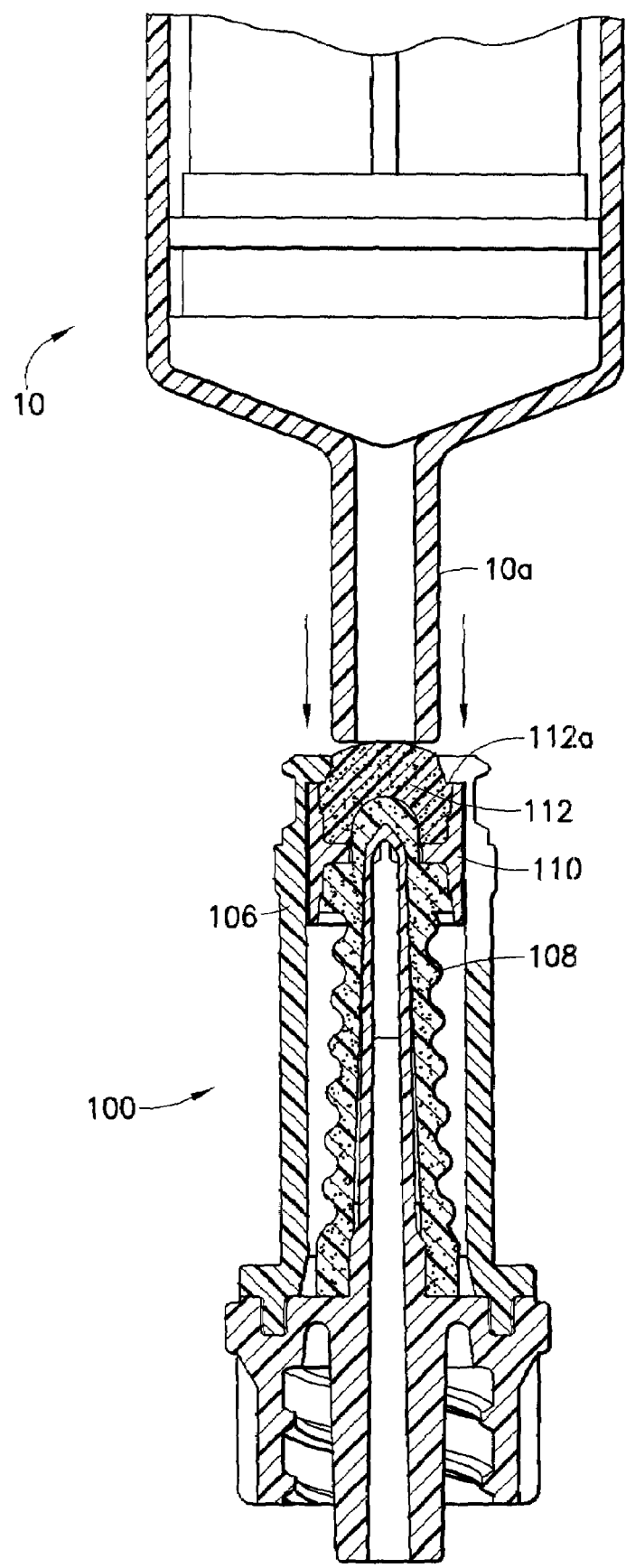
FIG. 4 is a broken longitudinal cross-sectional view of the assembled components of FIG. 2 and a standard male luer syringe positioned to activate the valve.
Figure 5:
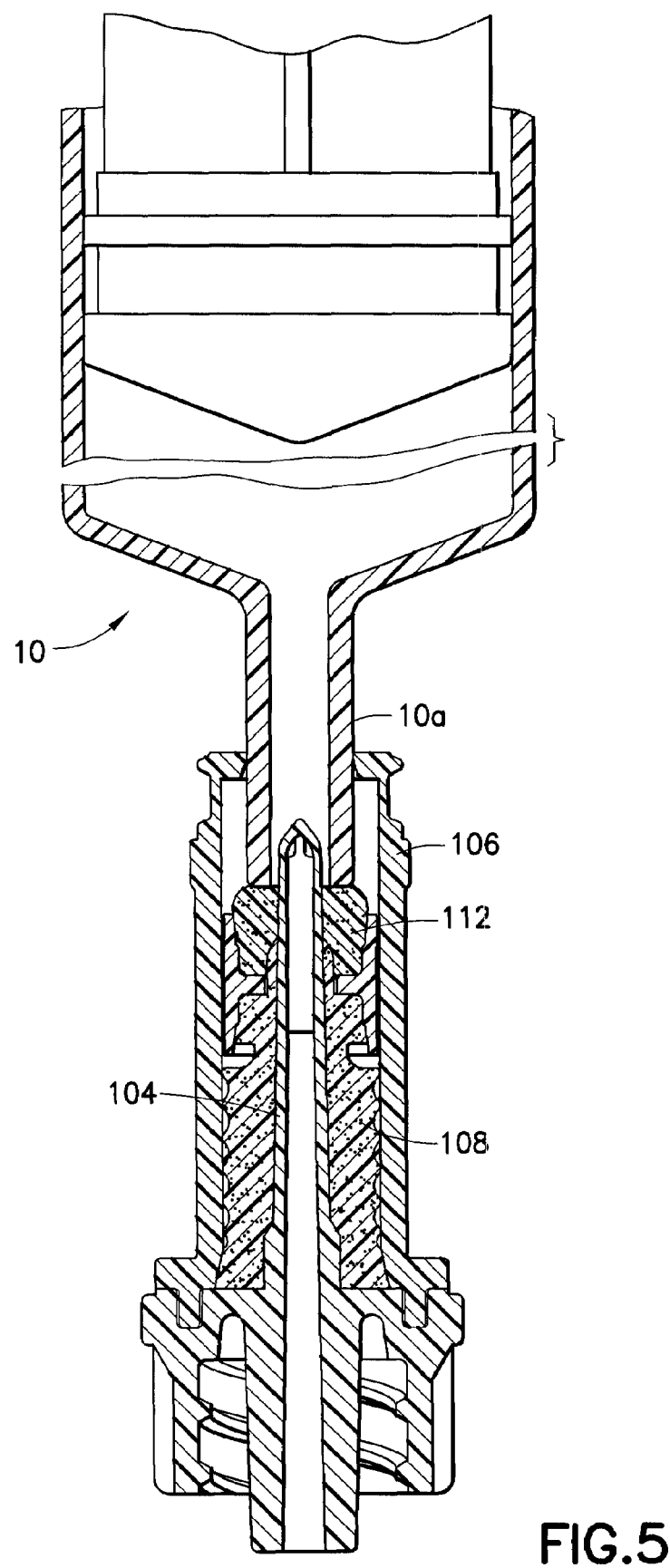
FIG. 5 is a view similar to FIG. 4 showing the valve activated by the standard male luer syringe.

Turning now to FIGS. 4 and 5, a needle-free syringe 10 has a male luer tip 10a which is matable with the female luer 106 of the invention. The male luer tip 10a is pressed against the swabbable surface 112a of the septum 112 and pushed down in the direction of the arrows shown in FIG. 4. As the male luer 10a is moved into the female luer 106, the septum 112 and the boot valve 108 are moved over the spike 104 as shown in FIG. 5. This opens a fluid path between the interior of the luer 10a and the interior of the spike 104 due to holes in the top of the spike as discussed below with reference to FIGS. 18-21.

Figure 6:
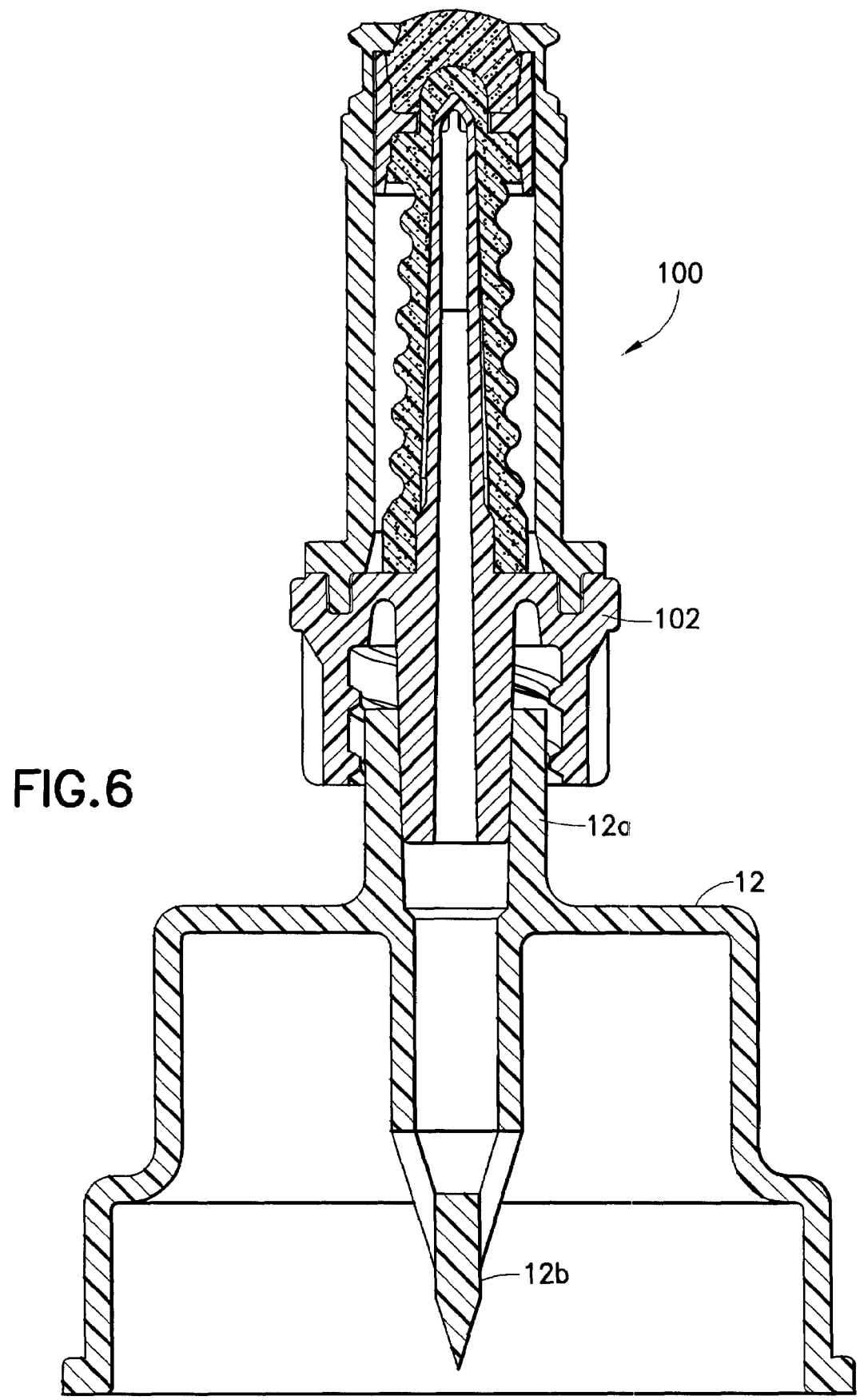
FIG. 6 is a view similar to FIG. 2 showing the assembled components in conjunction with a multiple-access drug vial adapter.

FIG. 6 illustrates how the invention can be used with a multiple access drug vial adapter 12. The drug vial adapter 12 has a female luer 12a at one end and a hollow spike 12b at the other end. The male luer 102 of the injection port system 100 engages the female luer 12a of the drug vial adapter and the spike 12b of the vial adapter pierces the septum of a drug vial (not shown).

Figure 7:
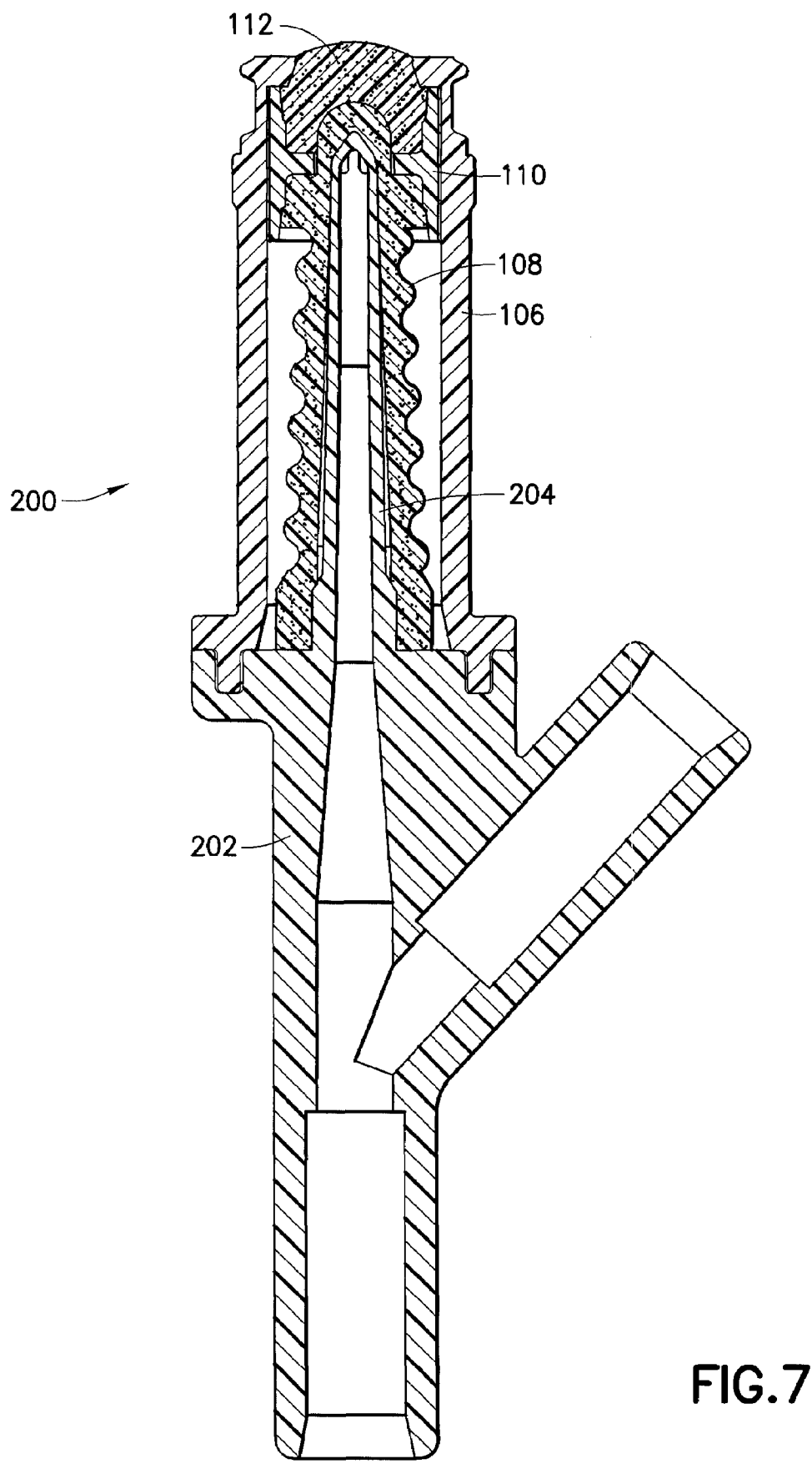
FIG. 7 is a longitudinal cross-sectional view of a Y-injection port according to the invention.

FIG. 7 illustrates a Y-site 200 incorporating an injection port according to the invention. The Y-site 200 has a Y-site base 202 which includes a spike 204 which is the same or similar to the spike 104 described above. The remaining components are the same as described above. Those skilled in the art will appreciate that the Y-site is useful when incorporated into an intravenous extension or administration set to allow injections via the same intravenous line through the injection port.

Figure 8:
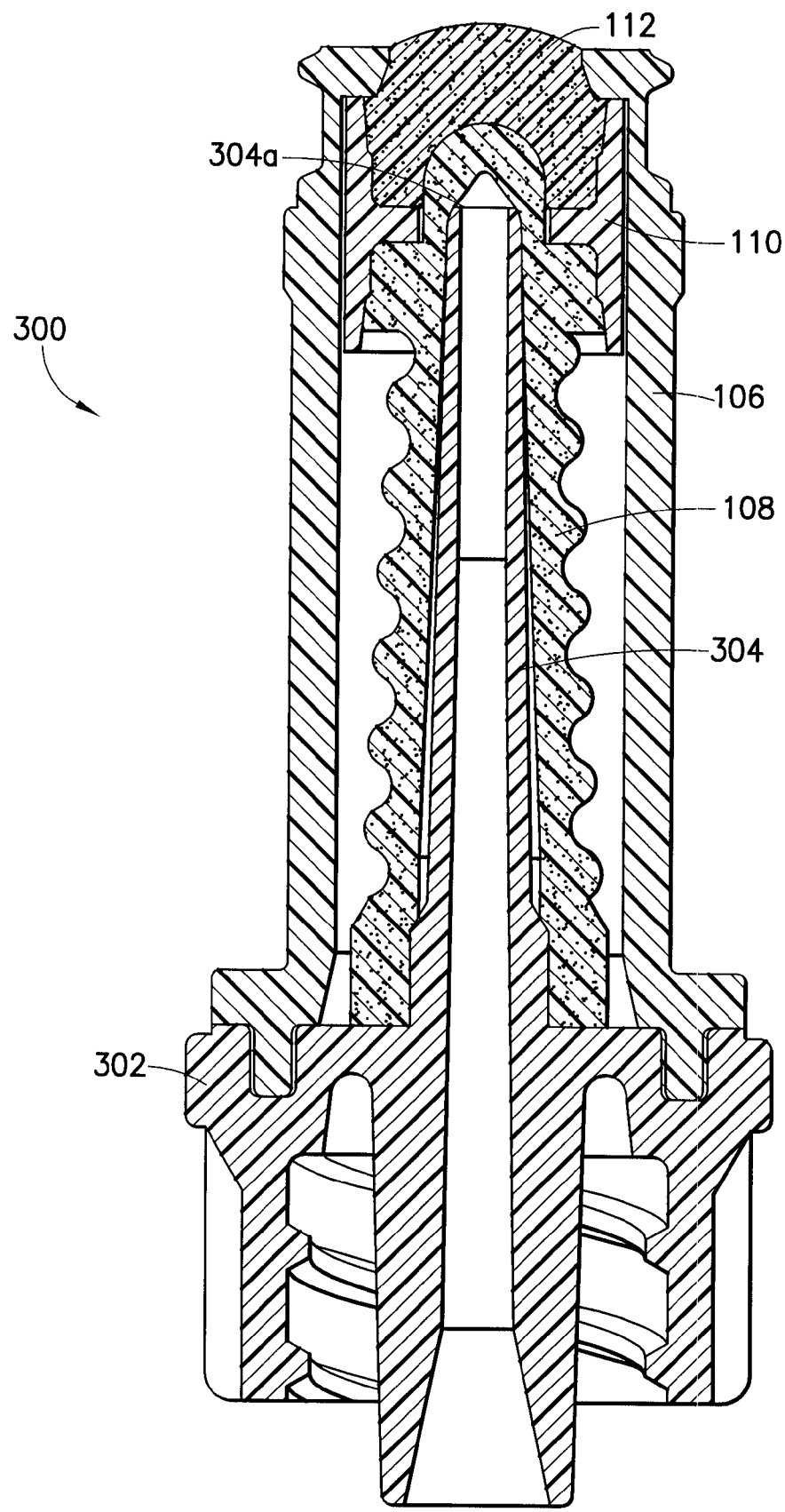
FIG. 8 is a view similar to FIG. 2 illustrating an alternate spike body.

FIG. 8 illustrates an alternate embodiment of an injection port 300. The injection port 300 has a spike body 302 with a spike 304 which does not have a point. It has, instead, an open tip 304a. The remainder of the components are the same as described above. This embodiment allows for the passage of guide-wires and other implements through the valve as described below with reference to FIGS. 23-25.

Figure 9:
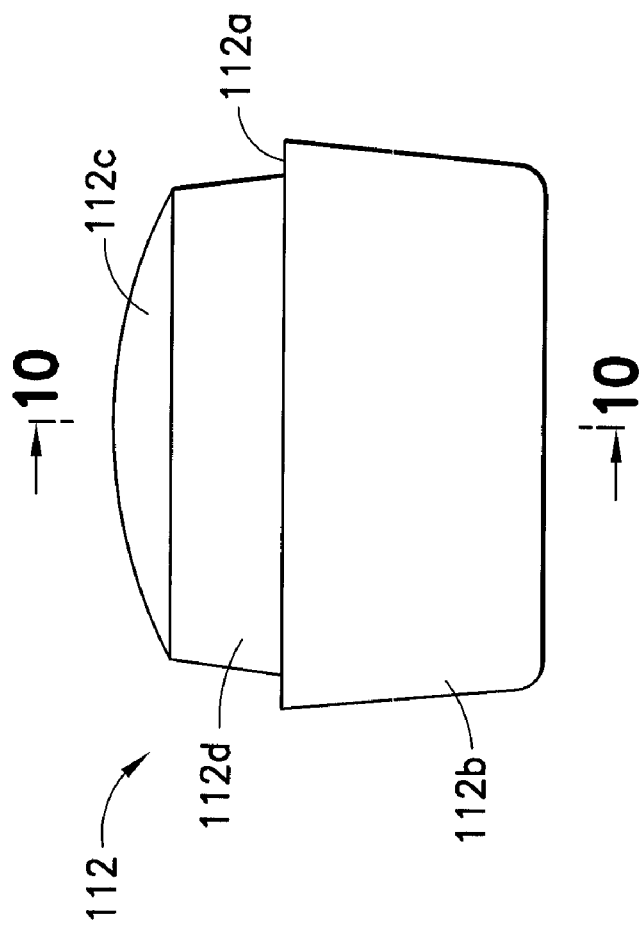
FIG. 9 is an enlarged side elevational view of a septum according to the invention.
Figure 10:
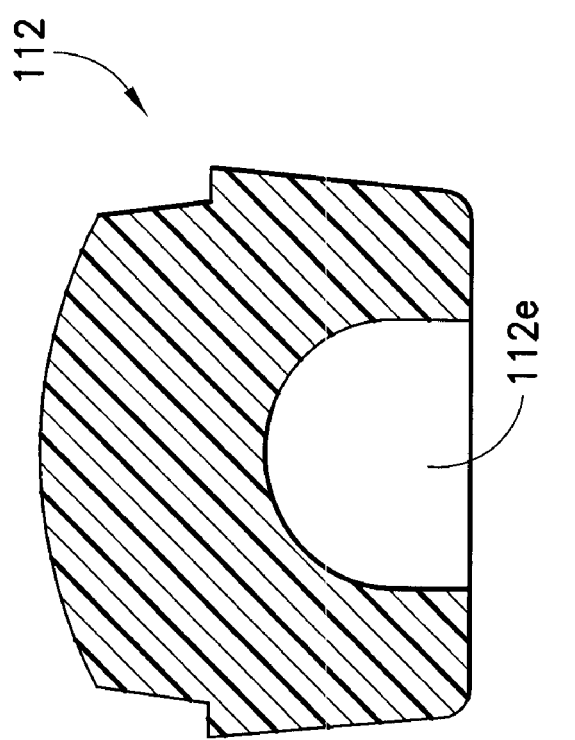
FIG. 10 is a section taken along line 10-10 in FIG. 9.

FIGS. 9 and 10 illustrate enlarged views of the septum 112. The septum 112 has an upper frustrum 112d and a lower frustrum 112b of larger diameter defining a shoulder 112a. The upper end of the upper frustrum 112d is a continuous convex surface 112c. The lower frustrum 112b defines a concavity 112e which is dimensioned to fit the tip of the boot valve with mechanical interference.

The upper resilient septum 112 provides the first line of defense against pathogen ingress into the fluid pathway from outside the injection port, and the second line of defense against fluid leakage due to high back pressure from inside the injection port. The septum is held in the "H-Guide" 110 as shown in FIG. 2 with a dimensional interference causing a circumferential mechanical force to assist in resealing the pre-puncture (not shown) in the center of the septum and boot valve during numerous activations. The outer shoulder or flange 112a has a larger diameter than the opening of the female luer component 106 and the upper frustrum 112d preferably makes an interference fit with the female luer opening as seen in FIG. 2.

As previously mentioned, the septum and boot valve are preferably pre-punctured prior to assembly of injection port with a lubricated piercing device. The pre-puncturing process is performed with the septum, H-guide, and boot valve sub-assembly and a piercing device which moves through the two independent and adjacent resilient barriers until the piercing device is totally through the sub-assembly. The piercing device, preferably a 0.056 inch width stainless steel knife blade (but other appropriate piercing devices would be acceptable), pre-punctures both the boot valve and septum in a smooth, in-line, axis geometry. This new smooth, in-line, axis geometry coupled with the fluorosilicone lubricant has reduced the required activation force to approximately 3.8 lbs, making it easier to use. This manufacturing process modification eliminates the jagged cuts, tears, and coring that was observed in the original process utilizing the internal spike tip. The piercing device is lubricated preferably with a fluorosilicone lubricant which assists in a smooth pre-puncture-axis geometry. The fluorosilicone formulation also minimizes the "cross-linking" of the silicone molecular structure during gamma radiation sterilization. It is understood that other FDA approved lubricants could be acceptable for this application. In addition, in order to improve the "snap-back" characteristics of this new injection port, and to minimize frictional abrasions within the boot valve during the compression or activation phase when the septum and boot valve move down over the internal spike tip and shaft, an inert lubricant is molded within the boot valve formulation. Synthetic polyisoprene and silicone are the preferable materials in this injection port due to their inertness, abrasive resistance, sealing and internal memory characteristics, and their sterilization capability. It is understood that other inert resilient materials could be used for this application.

Figure 13:
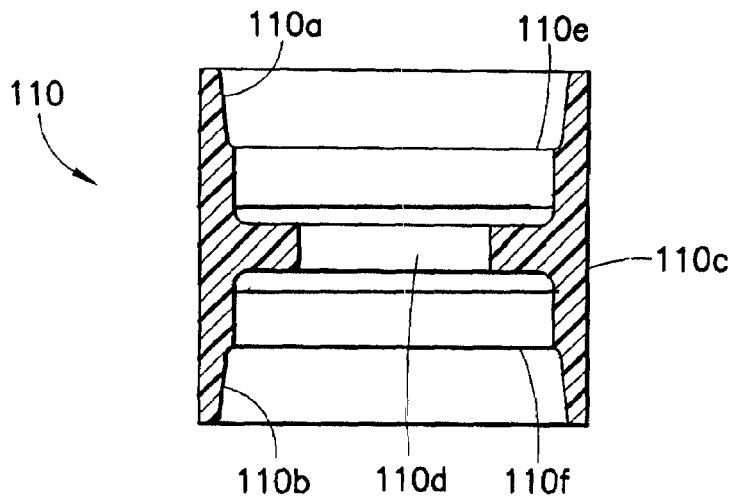
FIG. 13 is a section taken along line 13-13 in FIG. 11.
Figure 12:
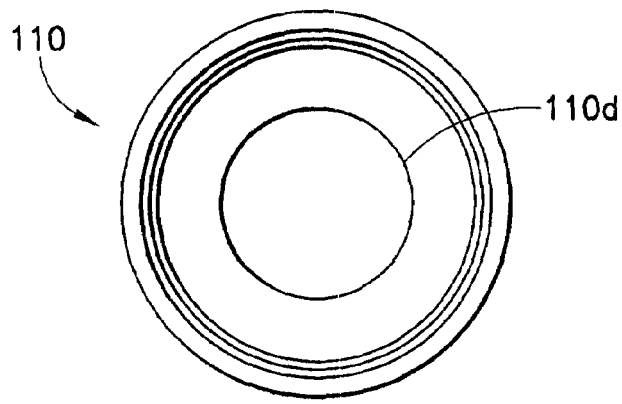
FIG. 12 is a top view of the H-guide of FIG. 11.
Figure 11:
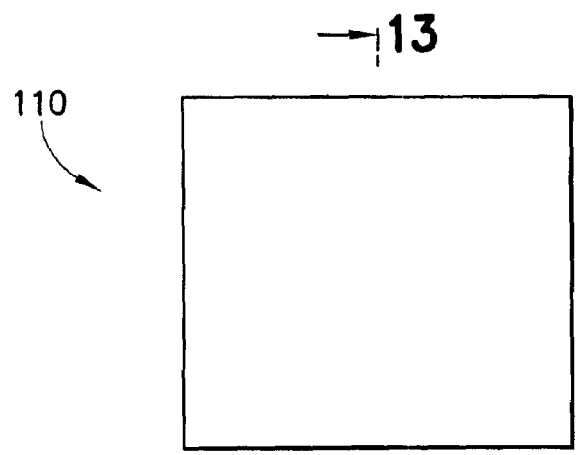
FIG. 11 is an enlarged side elevational view of an H-guide according to the invention.

Turning now to FIGS. 11-13, the H-guide centering member 110 includes a generally tubular outer portion 110c and an annular inner portion defining a hole 110d. The outer portion 110c is sized to stably axially slide within the central portion of the female luer component 106 as shown in FIG. 2. The outer portion 110c and inner portion together define first and second substantially identical receiving areas 110a, 110b. These areas have an outer tapered portion and an inner non-tapered smaller diameter portion. This assists in mating with the boot valve and the septum. The receiving areas 110a, 110b are preferably provided with annular rings 110e, 110f which assist in sealing the interface between the septum and the boot valve.

FIGS. 14 and 15 illustrate a second alternate embodiment of a boot valve. The difference between this embodiment and those described above is that undulations 208a are not helical but consist of a plurality of non-tapering projections arranged along the axis of the boot valve 208. Although this boot valve may not perform as well as the boot valve 108 in terms of snap back and activation force, it does retain the advantages of the frustrum 208b, the dimensions of the tip 208c, and the sealing ring 208d which helps seal the space between the boot valve and the spike shaft.

Figure 16:
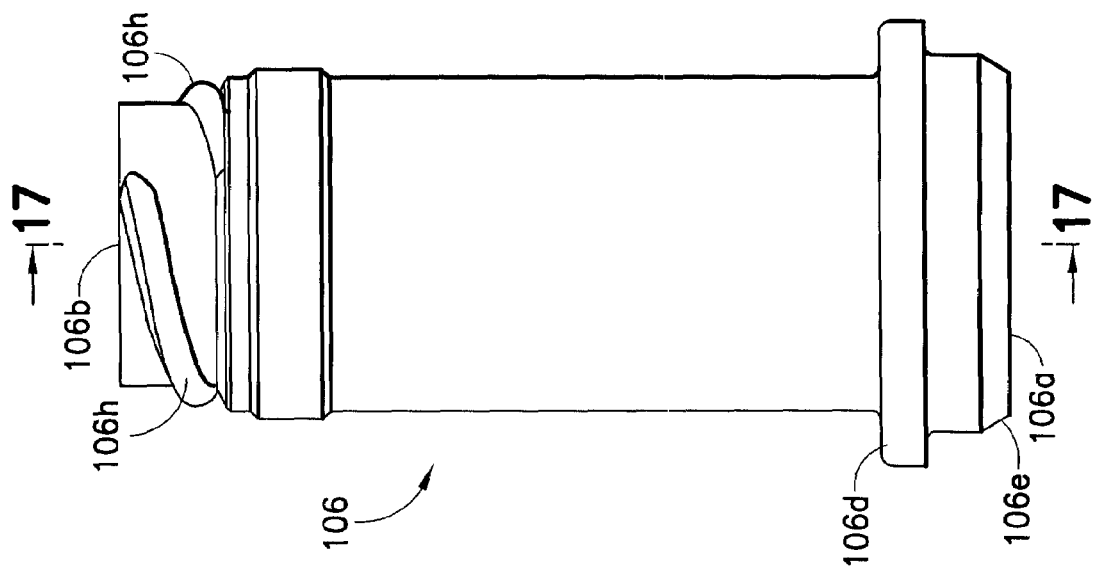
FIG. 16 is an enlarged side elevational view of a female luer body according to the invention.
Figure 17:
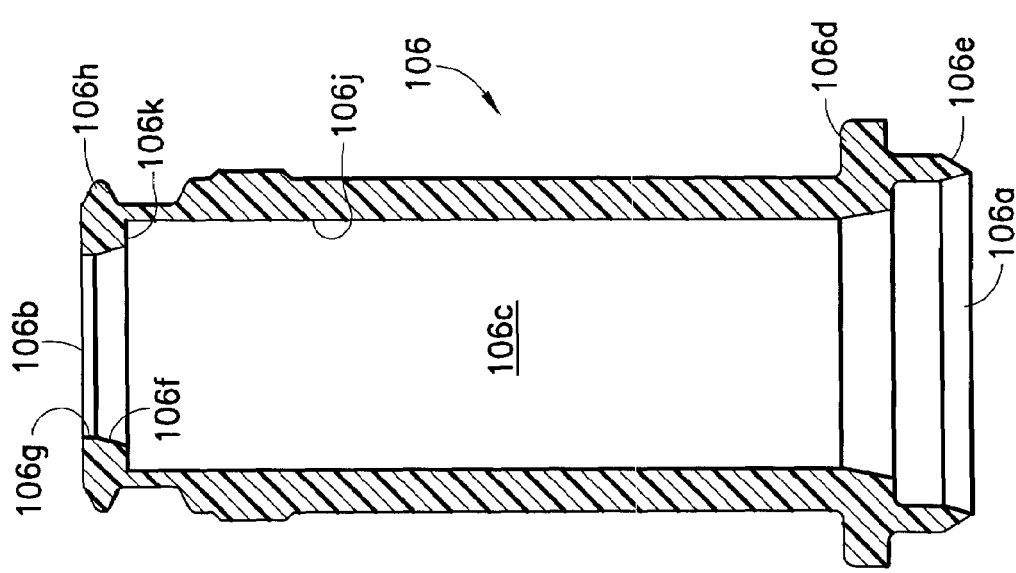
FIG. 17 is a section taken along line 17-17 in FIG. 16.
Figure 19:
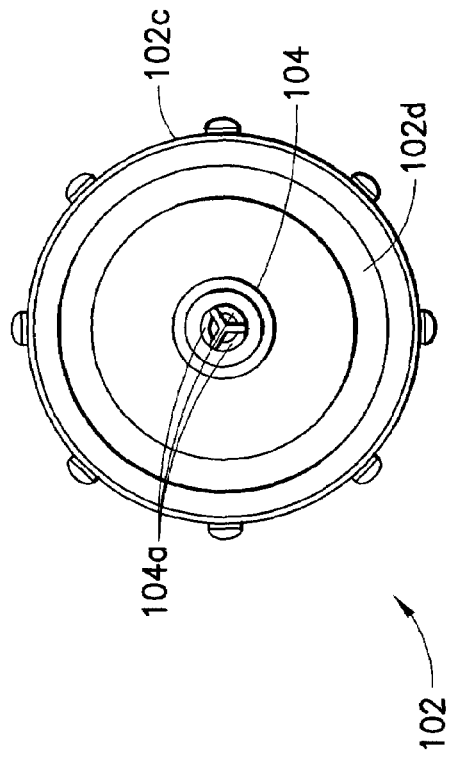
FIG. 19 is a top plan view of the spike body of FIG. 18.
Figure 20:
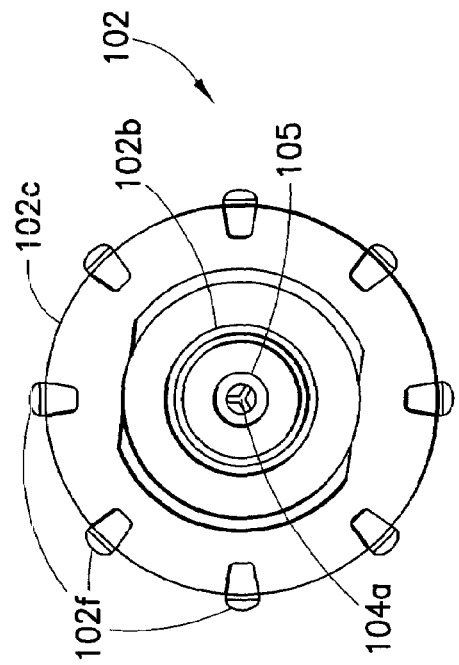
FIG. 20 is a bottom plan view of the spike body of FIG. 18.
Figure 18:
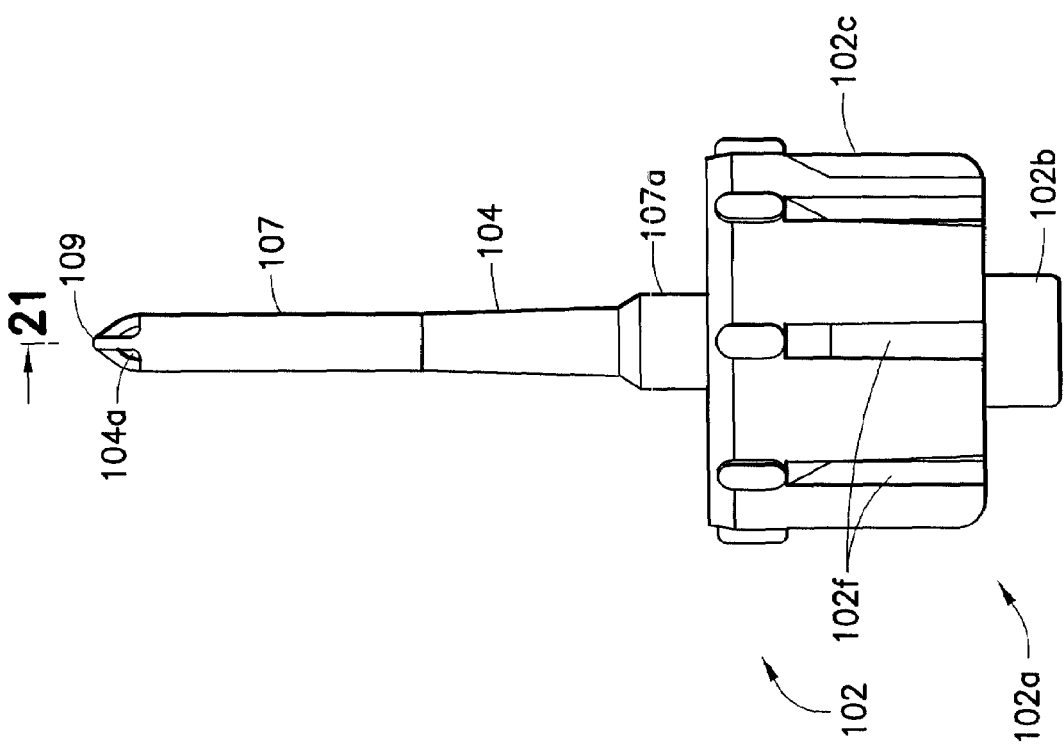
FIG. 18 is a side elevational view of a spike body according to the invention.
Figure 21:
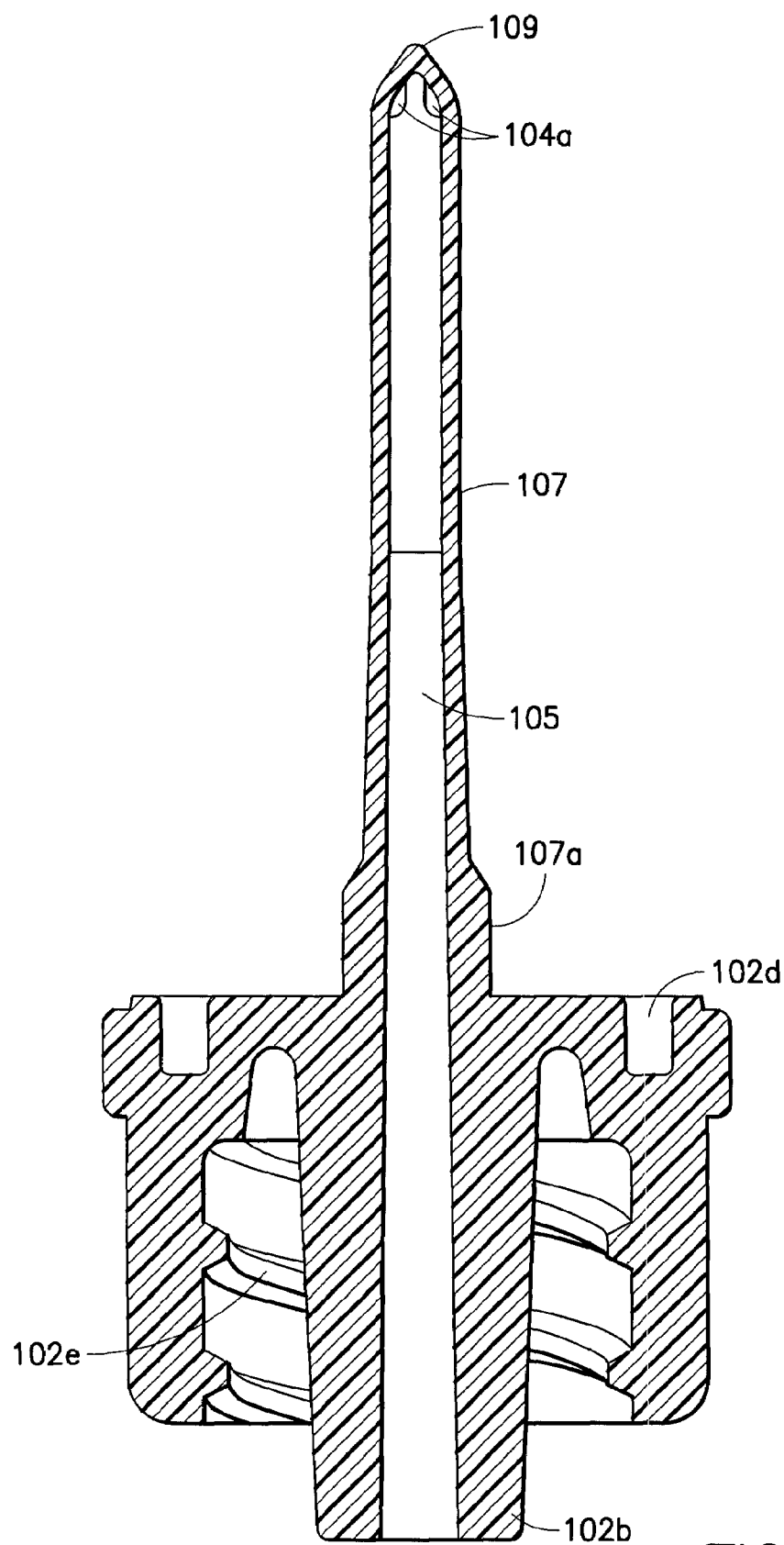
FIG. 21 is an enlarged section taken along line 21-21 in FIG. 18.

FIGS. 16 and 17 illustrate enlarged views of the female luer component 106. The female luer connector component 106 is tubular and includes a first open end 106a, a female luer second end 106b, and a central portion 106c therebetween. The first end 106a includes a flange 106d which is preferably provided with an annular mating ridge 106e. The ridge defines an enlarged diameter relative to the central portion 106c, and is provided on the flange 106d directed away from the second end 106b. The mating ridge 106e is sized and shaped to be received in the annular mating slot of the spike body 102 (described below with reference to FIGS. 19 and 21). The second end 106b includes an opening having a reduced (relative to the rest of the component 106) with a tapered portion 106f and a non-tapered portion 106g. The tapered and non-tapered portions provide a better sealing fit with the septum 112 as shown in FIG. 2. A luer lock thread 106h is preferably provided about the second end 106b.

The internal wall 106j of the component 106 is preferably smooth and slightly tapered up to a perpendicular wall 106k, leading to an opening approximately 0.180 inch diameter which preferably tapers to approximately a 0.164 inch diameter in the second end 106b of the female luer body component. The internal wall is preferably smooth to allow the H-guide component to axially move without obstruction during the compression and snap-back phases. It is understood, that a fluted internal wall structure could also be acceptable.

FIGS. 18 through 21 illustrate the spike body 102 in greater detail. The spike body includes a first end 102a having a male luer connector 102b, the spike 104 preferably integrally formed with the body 102 and coaxially directed opposite the male luer connector 102b, and a base 102c at the juncture of the male luer connector 102b and the spike 104. A fluid path 105 is provided through the spike 104 and male luer connector 102b. The spike 104 has a tapered shaft 107 leading to a bullet-nose arched tip 109 which defines a second end of the spike body 102. The tip 109 includes a plurality of slots (e.g., three slots) 104a which provide access into the hollow 105 of the spike 104 from outside the spike. The shaft 107 includes a base portion 107a which has an enlarged stepped diameter for holding the boot valve thereabout. The base 102c of the spike body 102 also includes an annular groove 102d which receives the mating ridge 106e of the female luer component 106. The base 102c preferably also includes a plurality of internal threads 102e which together with the male luer connector 102b function as a male luer lock. In addition, the periphery of the base 102c includes a plurality of molded longitudinal ridges 102f to facilitate engagement of the periphery of the spike body by human fingers.

As mentioned above, a preferred embodiment of the integral spike shaft and spike tip used in the present invention is configured with a roughened finish external surface and a fluorosilicone liquid lubricate used along the shaft and tip. The roughened finished external surface creates a roughened surface with approximately 0.001 to 0.002 inch depth areas allowing for a circumfluent flow of the liquid lubricant along the spike shaft and spike tip. The previously incorporated co-owned invention had a very smooth external spike shaft surface with a Dow 360 silicone lubricant. This smooth surface caused on occasion a "suction" affect between the internal wall surface of the boot valve component and the spike shaft. The roughened finish allows the lubricant to flow into the 0.001-0.002 inch impressions on the spike shaft, eliminating the "suction" effect seen in the prior invention, and maintaining adequate lubrication between the internal wall of the boot valve and spike shaft during numerous compression and snap-back cycles of the valve. This surface improvement also enhances the "snap-back" feature of the valve.

From the foregoing, it will be appreciated that the female luer 106, the septum 112, the H-guide 110, the boot valve 108, and the spike 104 interact as described below to obtain numerous advantages. The septum 112, by being properly dimensioned and entrapped within the female luer component when in the assembled slightly compressed state passes a 30 psi backpressure test, thus improving the prevention of fluid leakage from the injection port. It also provides a primary seal surface to further prevent gross particulate contamination from entering into the body of the injection port, thus preventing pathogen ingress into the patient's blood stream. Further, the interference fit between the septum and the female luer increases the circumferential mechanical force to improve the resealing of the pre-puncture in the center of the septum in the assembled slightly compressed state. In addition, as discussed below, these elements help assist in obtaining a zero fluid displacement for the assembly.

The taper of the lower frustrum 112b assists in the assembly of the septum in the H-guide 110. The lower frustrum 112b also has a larger diameter than the matching inside wall diameter of the H-guide causing a mechanical interference. This mechanical interference frictionally holds the septum into the H-guide.

The interior cavity 112e of the septum has a matching contour to the tip of the boot valve 108. The diameter of this cavity is smaller than the tip of the boot valve, causing a circumferential mechanical fit against the pre-puncture in the boot valve. This new design eliminates any interstitial cavity chamber or dead space between these two interfaces thus assisting in achieving a "zero fluid displacement" when the valve is moved from the assembled slightly compressed state to the compressed state and vice versa. The interference fit between the septum and the tip of the boot valve also improves the performance of the injection port in the assembled slightly compressed state in the following ways. There is improved resealing of the pre-puncture in the center of the boot valve, improved prevention of pathogen ingress into the patient's bloodstream through the pre-puncture in the boot valve, and improved prevention of fluid leakage from the patient's side of the injection port.

Another design modification that improves the overall performance of this new injection port is the provision of a single continuous swabbable surface on the proximal side of the septum. In addition, all of the external surfaces of the septum that come in contact with the H-Guide and the boot valve are smooth to assist in the sealing characteristics between these component interfaces.

The new H-guide centering component assists in the new design enhancements and improvements. The H-guide contains both the upper resilient septum and the lower resilient boot valve. The outer diameters of the septum and the boot valve are larger than the inner wall diameters of the H-guide where they interface, giving a frictional interference fit between all components. The H-guide centering component is also shaped similar to the lead-in tapers of the septum and the boot valve for ease of assembly. The dimensional mechanical interference between the septum and the H-guide applies a mechanical pressure against the pre-puncture axis of the two independent and adjacent resilient barriers, thereby improving microbial ingress prevention, improving fluid leakage prevention, and assisting in eliminating the dead space between the septum/boot valve and boot valve/spike tip interfaces to achieve zero fluid displacement during the compression and snap-back cycle. The H-guide also prevents the two resilient barriers from coming in contact with the female luer inner wall, thereby eliminating any frictional abrasion during the compression and snap-back cycle of the resilient barriers rubbing against the inner wall of the female luer body element, thereby, improving the snap-back capability of the valve. The H-guide also keeps the septum and boot valve in-line puncture axis geometry "centered" over the stationary spike tip and shaft, preventing jagged cuts, tears, or coring of the two resilient barriers. The outer diameter of the H-guide is slightly smaller than the inside diameter of the female luer body, allowing for a smooth axial movement of the valve during compression and snap-back cycle. A preferred material for the H-guide is high-density polyethylene due to its lubricity characteristics, but other plastic materials could function in this application.

Figure 22:
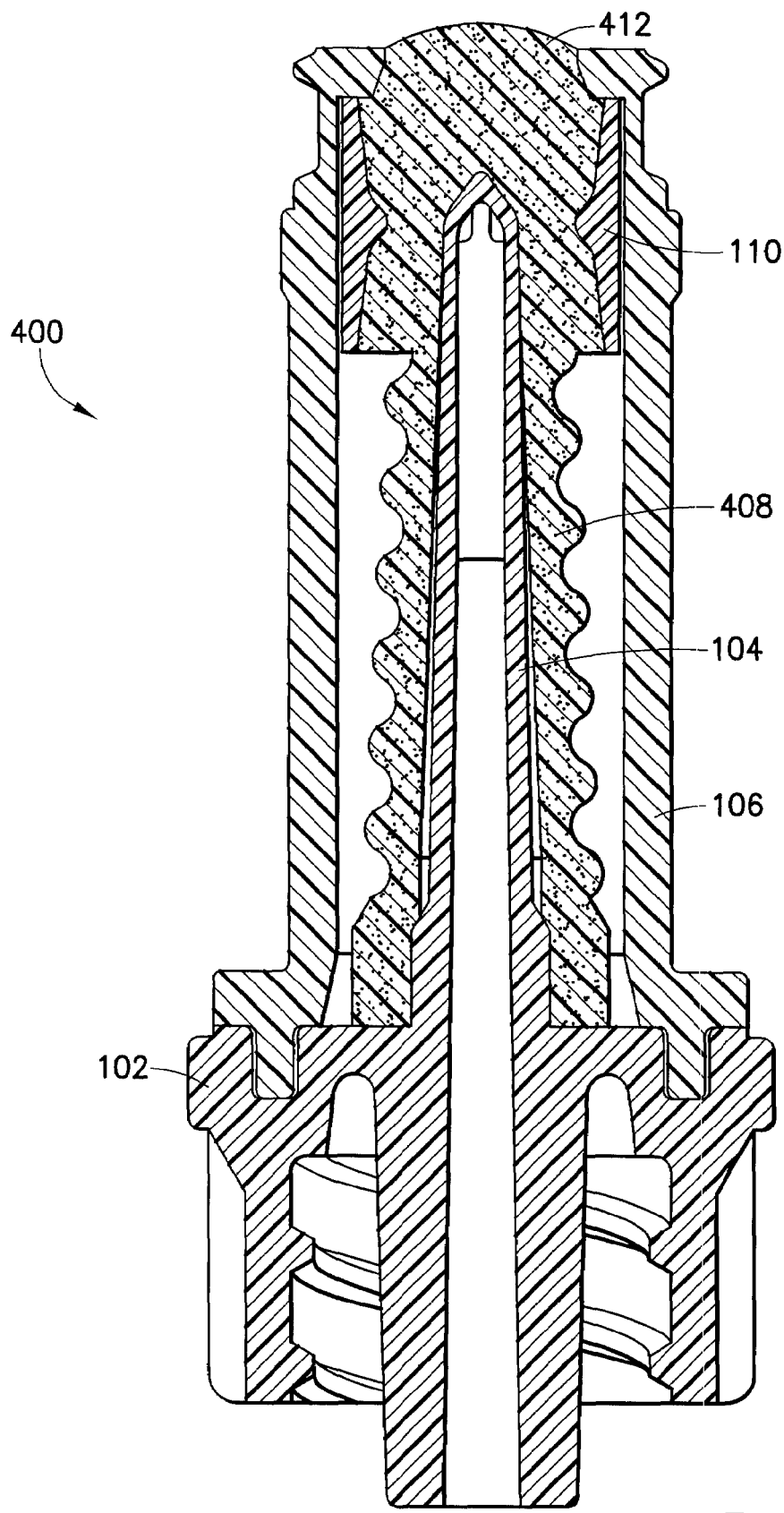
FIG. 22 is a view similar to FIG. 2 illustrating a single piece combination septum and boot valve.

FIG. 22 illustrates another embodiment of an injection port 400 according to the invention. This embodiment differs from the first embodiment in that the boot valve 408 and the septum 412 are a single piece. All of the other components are the same as the first embodiment.

Figure 24:
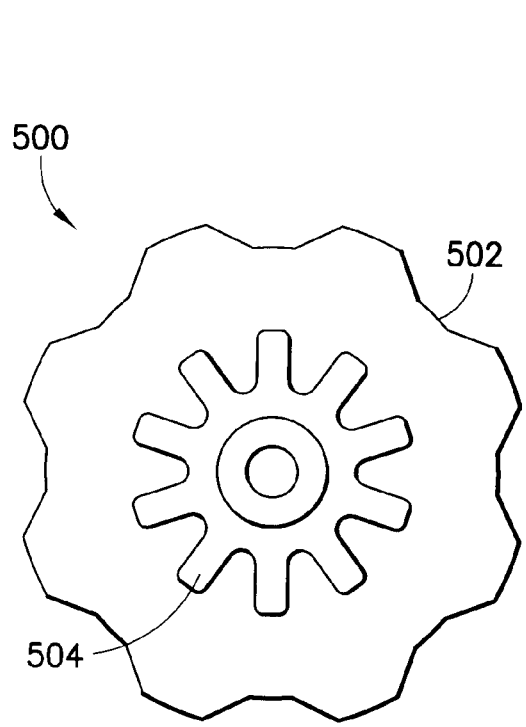
FIG. 24 is a top plan view of the guide wire adapter of FIG. 23.
Figure 23:
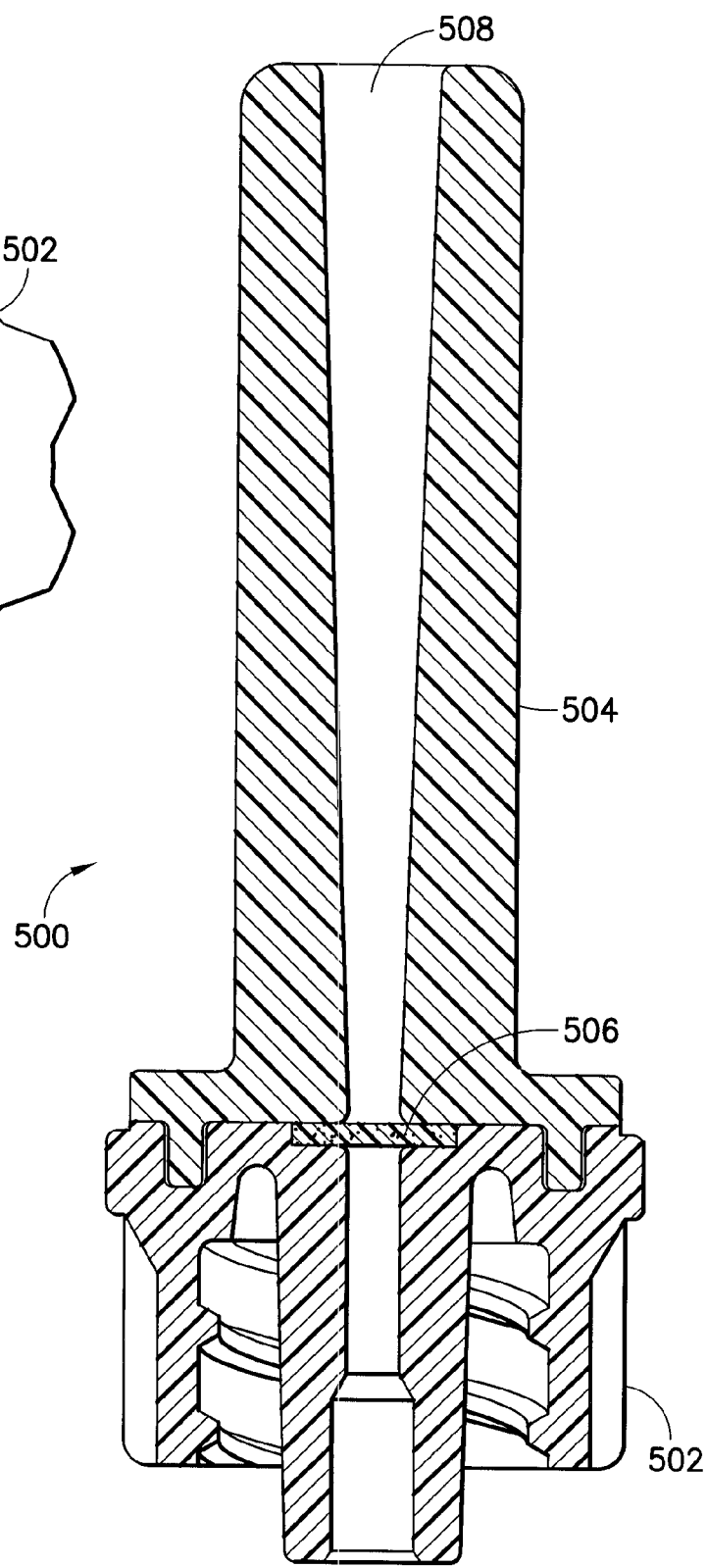
FIG. 23 is a longitudinal sectional view of a guide wire adapter for use with the injection port system of the invention.
Figure 25:
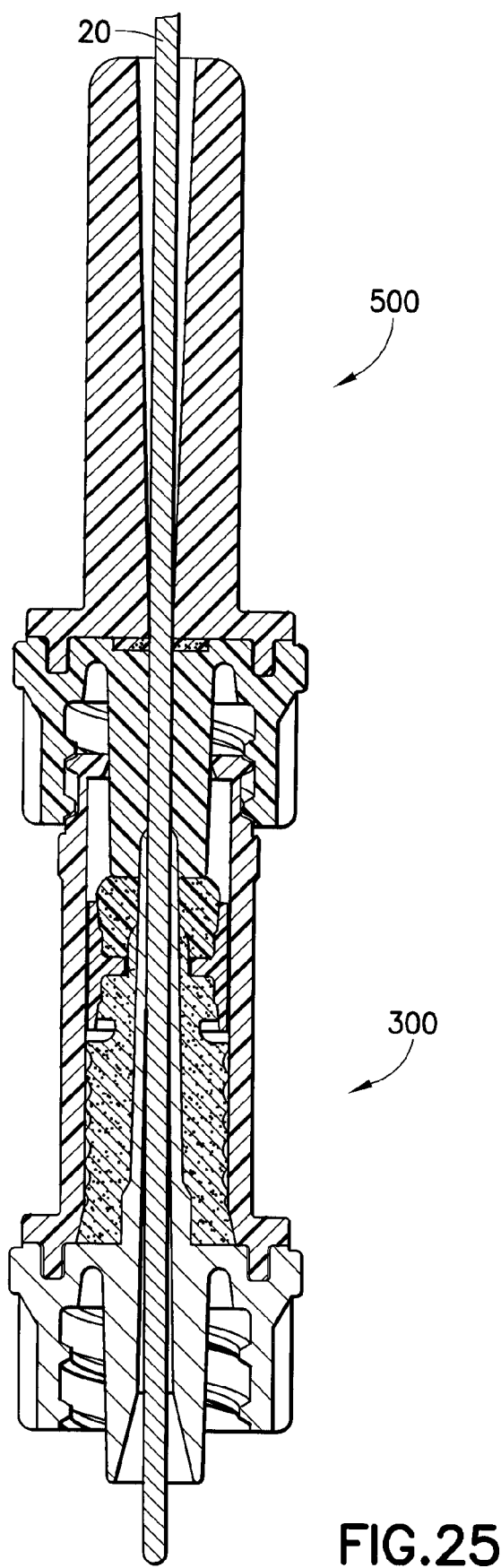
FIG. 25 is a longitudinal sectional view of the guide wire adapter of FIG. 23 coupled to an injection port system of the invention.

FIGS. 23 and 24 illustrate a guide wire adapter for use with an injection port according to the invention. The guide wire adapter 500 includes a male luer base 502 and an elongated female luer body 504 coupled to the male luer base with a thin silicone resilient disk 506 therebetween. The disk is preferably pre-punctured in its center. The silicone disk prevents air ingress into the patient's blood stream and prevents blood egress from the device during guide-wire applications. The female luer body 504 has a tapered inner bore 508 which is coaxial with the bore of the male luer 502. The exterior of the female luer body 504 is fluted as shown in FIG. 24. When the guide wire adapter 500 is coupled to an injection port 300 of FIG. 8 as shown in FIG. 25, a guide wire 20 may be inserted through the adapter into and through the injection port.

Figure 26:
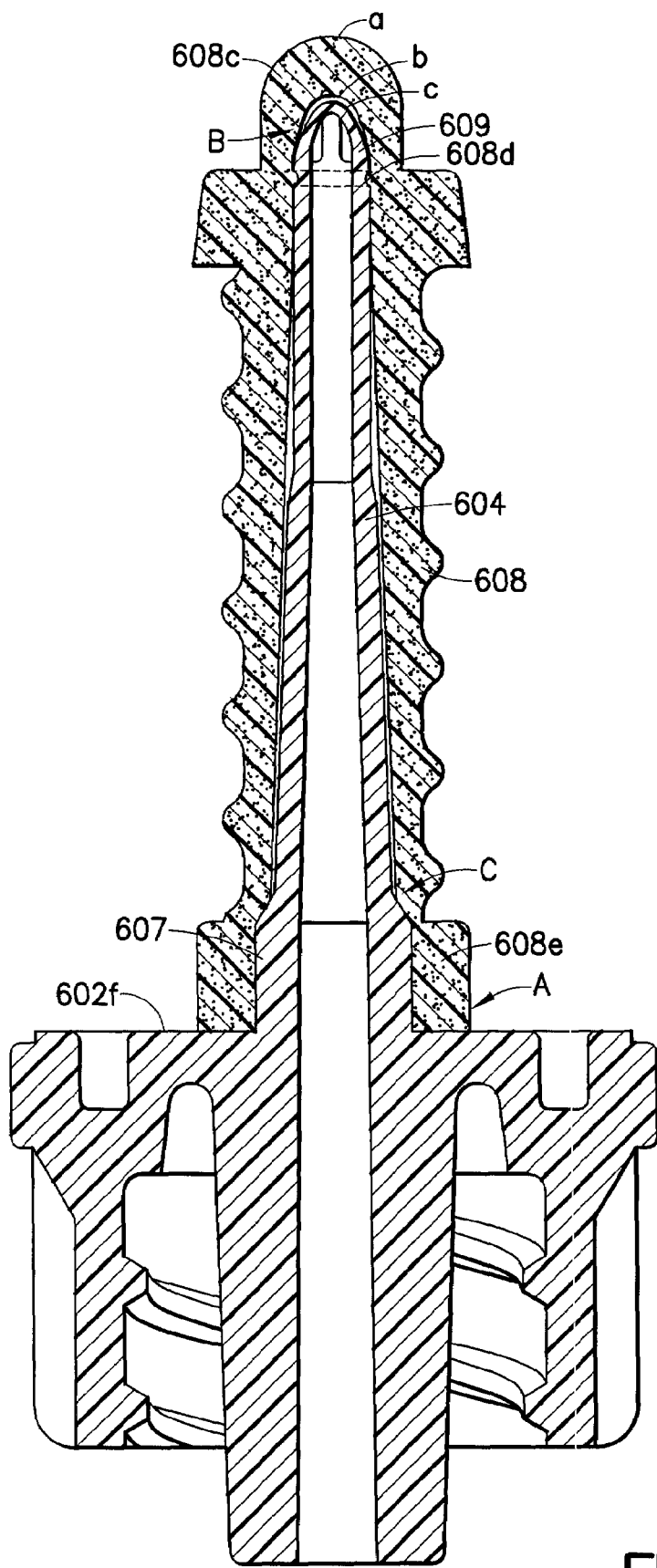
FIG. 26 is a longitudinal cross-sectional overlay of a spike body and a boot according to another embodiment of the invention.

Turning now to FIG. 26, another embodiment of the boot and spike of the invention is seen. In FIG. 26, the boot 608 and spike 604 are shown in their preassembled state as an overlay of each other. Thus, at the area designated A, the base 608e of the boot is shown extending down below (interfering with) the top surface 602f of the lower luer portion of the spike, whereas, in reality, when assembled, the base 608e of boot 608 must rest atop the surface 602f with the inner surface of the boot frictionally fitting on the widened base 607 of the spike (see, e.g., FIG. 2). Similarly, at the area designated B, the tip 609 of spike 604 interferes with the tip 608c of boot 608. This is best appreciated by understanding that the outer line marked "a" is the outer surface of the boot 608; the next line inward from line a is marked "b" and is the top of tip 609 of the spike; and the next line marked "c" is the interior surface of the tip 608c of boot 608. When assembled, the spike tip will be within the boot (see, e.g., FIG. 2) and there will be no gap between the spike tip and the boot tip. A third area of interference seen is at the area designated C. However, when the boot 608 is placed on the top surface 602f of the lower luer portion of the spike, that interference disappears. In fact, a small clearance is provided between the spike and the boot along the length of the spike between the base 607 of the spike and the sealing ring 608d in the tip area 609. This clearance permits the boot to be relatively easily compressed without much friction when the tip 608c of the boot 608 is forced over the spike tip during use.

Turning now to FIGS. 27-30A and 30B in conjunction with FIG. 26, it will be appreciated that boot 608 is a helically threaded boot as in the other embodiments of the invention. However, boot 608 differs from the other helically threaded boots in three manners. First, as seen best in FIGS. 28 and 29, the outer surface 608a of the threaded portion of the boot 608 does not taper at all. In fact, any horizontal cross-section through the threaded portion of the boot 608 will show that the distance from one side of the boot to the other is constant. Second, as seen best in FIGS. 30A and 30B, the inside surface of the threaded portion of the boot is configured as an octagon (although other polygons such as a hexagon, pentagon, square, etc. could be utilized) such that there is effectively no diameter to the inside and such that the points of contact during compression of the boot over the spike are reduced. It is noted that the tip portion of the boot maintains its circular inside surface. Third, as seen best in FIGS. 26 and 29, the wall thickness of the boot generally increases as the boot goes from its base toward its tip. Thus, just above its base, the octagonal area bounded by the inside surface of the boot (FIG. 30B) is larger than the octagonal area bounded adjacent the tip (FIG. 30A). It has been found that the boot 608 provides less resistance to the mating connection of a syringe luer to the injection port valve system of the invention (i.e., a lower activation force by approximately 50% relative to the boot of previously incorporated U.S. Pat. No. 6,113,068), and provides better snap-back action.

Another difference between the embodiment of FIG. 26 and other embodiments is that the spike 604 does not taper much towards its tip end, and then has a middle section which flares outwardly. This arrangement permits the assembly to be used with mini-volume extension sets (used with IV syringe pumps). Other aspects of the boot 608 and spike 604 are the same as in the other embodiments. For example, the boot and spike are made of the same materials as disclosed with reference to the other embodiments, the surface of the spike 604 is preferably roughened and is coated with a fluorosilicone lubricant, etc. With the spike and boot of FIG. 26, a zero fluid displacement system is obtained with a connection displacement of 0.000 mL-0.000 and +0.002 mL and a detachment displacement of 0.000 mL±0.000 mL.

There have been described and illustrated herein several embodiments of medical intravenous administration injection ports. While particular embodiments of the invention have been described, it is not intended that the invention be limited thereto, as it is intended that the invention be as broad in scope as the art will allow. Thus, it will be appreciated by those skilled in the art that the term "intravenous fluid" is intended to be understood in a broad sense to include parenteral fluids including drug solutions, blood, blood products, dyes, or other fluids and the term "administration" is used in its broad sense to include the dispensing or collection of the "intravenous fluid". Further, while the injection port is illustrated as preferably having a female luer lock on one end, and a male luer lock on the other end, it will be appreciated that, although not preferred, simple luer slips could be utilized in lieu of luer locks. Furthermore, while a ridge and groove are disclosed for mating the female luer component and spike body together, it will be appreciated that other mating means may be used. For example, a plurality of mating tabs and slots, or ridges and grooves, or the like, may be used. Moreover, while a particular plastic material has been disclosed for the spike body, female luer component, and centering member, it will be appreciated that other rigid materials may likewise be used for these components. Also, in each embodiment the spike may be unitary with or of a separate construction than the body. Furthermore, while particular rubber-like materials have been disclosed for the boot valve and septum, it will be appreciated that other rubber-like materials of different Durometers may also be used. Further yet, while the boot valve and septum are described as preferably being pre-punctured with a knife blade, it will be appreciated that, if desired, neither the boot valve nor the septum need be pre-punctured, or only one of them might be pre-punctured, and that they may be pre-punctured with a solid core needle or other means. Alternatively, although not preferred, the boot valve and/or septum may be pre-slit; i.e., injection molded with a horizontal slit therein. Pre-slitting the boot valve and/or septum is not preferred as during use the pre-slit boot and/or septum will not accommodate the spike as well as a pre-punctured boot and/or septum. It will therefore be more prone to tearing, thereby leaving the pre-slit device more prone to undesirable microbial migration. Also, while a boot valve having an outer helical surface and a linear and tapered inner surface has been shown, it will be appreciated that the boot valve could also have a helical inner or other non-linear or non-tapered surface. Therefore, it will be appreciated by those skilled in the art that yet other modifications could be made to the provided invention without deviating from its spirit and scope as so claimed.

The invention claimed is:

1. An injection port assembly for coupling to and uncoupling from a first fluid pathway of a first connector and for coupling to a device provided with a second connector so as to provide a fluid connection between the first and second connectors, said injection port assembly comprising:
   a body having a first mating structure adapted to mate with the first connector and a second mating structure coupled to said first mating structure and adapted to mate with the second connector,
   a resilient barrier substantially contained within said body and compressible from a first position in which fluid flow between said first mating structure and said second mating structure is blocked to a more compressed second position in which fluid flow between said first mating structure and said second mating structure is permitted,
   said resilient barrier having a generally helical outer surface pattern and a regular polygonal inner surface along at least a portion of its length.

2. An injection port assembly according to claim 1, further comprising:
   said resilient barrier includes a boot valve totally contained within said body and a septum at least mostly contained within said body.

3. An injection port assembly according to claim 2, further comprising:
   a spike coupled to said body and mounted within said resilient barrier.

4. An injection assembly according to claim 3, wherein:
   said spike has a roughened surface which is covered with a lubricant.

5. An injection port assembly according to claim 2, wherein; said boot valve and said septum are mated with mechanical interference.

6. An injection port assembly according to claim 1, wherein:
   said resilient barrier has a tip portion having a circular inner surface.

* * * * *